(12) United States Patent
Lal et al.

(10) Patent No.: US 11,603,429 B2
(45) Date of Patent: Mar. 14, 2023

(54) PHENALKAMINE EPOXY CURING AGENTS AND EPOXY RESIN COMPOSITIONS CONTAINING THE SAME

(71) Applicant: Evonik Operations GmbH, Essen (DE)

(72) Inventors: Gauri Sankar Lal, Whitehall, PA (US); Michael Cook, Macungie, PA (US); Gamini Ananda Vedage, Bethlehem, PA (US); Emmanouil Roumpelakis, Breinigsville, PA (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/041,500

(22) PCT Filed: Mar. 29, 2019

(86) PCT No.: PCT/EP2019/058033
§ 371 (c)(1),
(2) Date: Sep. 25, 2020

(87) PCT Pub. No.: WO2019/185876
PCT Pub. Date: Oct. 3, 2019

(65) Prior Publication Data
US 2021/0047461 A1  Feb. 18, 2021
US 2021/0355270 A9  Nov. 18, 2021

Related U.S. Application Data

(60) Provisional application No. 62/650,376, filed on Mar. 30, 2018.

(30) Foreign Application Priority Data

Mar. 26, 2019  (WO) ................ PCT/EP2019/057481

(51) Int. Cl.
| C08G 59/50 | (2006.01) |
| C07C 213/00 | (2006.01) |
| C07C 215/50 | (2006.01) |
| C08G 59/32 | (2006.01) |
| C09D 163/00 | (2006.01) |
| C09J 163/00 | (2006.01) |

(52) U.S. Cl.
CPC ........ C08G 59/5033 (2013.01); C07C 213/00 (2013.01); C07C 215/50 (2013.01); C08G 59/3218 (2013.01); C09D 163/00 (2013.01); C09J 163/00 (2013.01)

(58) Field of Classification Search
CPC ........... C08G 59/5033; C08G 59/3218; C07C 213/00; C07C 215/50; C09D 163/00; C09J 163/00
USPC ...................................................... 528/407
See application file for complete search history.

(56) References Cited

U.S. PATENT DOCUMENTS

| 4,981,889 A | 1/1991 | Baba et al. |
| 5,130,402 A | 7/1992 | Akiyama et al. |
| 6,262,148 B1 | 7/2001 | Cheng et al. |
| 2014/0107313 A1* | 4/2014 | Burckhardt ............. C08L 63/00 528/87 |
| 2017/0240691 A1 | 8/2017 | Zheng et al. |

FOREIGN PATENT DOCUMENTS

| CN | 103102506 A | 5/2013 |
| CN | 107663268 A | 2/2018 |
| EP | 0214495 A2 | 3/1987 |
| EP | 2108668 A1 | 10/2009 |
| GB | 1529740 A | 10/1978 |
| WO | 0001659 A1 | 1/2000 |
| WO | 2009080209 A1 | 7/2009 |
| WO | 2014067096 A1 | 5/2014 |
| WO | 2015085461 A1 | 6/2015 |
| WO | 2015153399 A1 | 10/2015 |
| WO | 2017140687 A1 | 8/2017 |

OTHER PUBLICATIONS

PCT International Search Report dated Jul. 8, 2019 corresponding to PCT Application No. PCT/EP2019/058033 filed Mar. 29, 2019 (13 pages).
Emilie Darroman et al.: "New aromatic Amine based on cardanol giving new biobased epoxy Networks with cardanol: Amine functionalized cardanol for epoxy resins", European Journal of Lipid science and Technology, vol. 117, No. 2, Oct. 16, 2014, pp. 178-189, XP55599696.
Antonio Greco et al.: "Use of cardanol derivaties as plasticizers for PVC : Cardanol dervived PVC plasticizers", Journal of vinyl and additive Technology, vol. 24, 2016, pp. E62-E70, XP55581996, US.

* cited by examiner

Primary Examiner — David T Karst
(74) Attorney, Agent, or Firm — Andrew H. Chung; Linda S. Li; Jason S. Ngui

(57) ABSTRACT

The present invention relates to a new structural class of phenalkamines, curing agent compositions comprising the phenalkamines, their use, as well as and methods of producing such phenalkamines and compositions. The phenalkamines of the present invention can be prepared by reacting cardanol with an aldehyde compound and triaminononane. These curing-agent compositions may be used to cure, harden, and/or crosslink an epoxy resin. The curing-agent compositions of this invention are of low viscosity and can be used neat or dissolved in a minimum amount of an organic solvent or diluent to effect cure of epoxy resins.

19 Claims, No Drawings

PHENALKAMINE EPOXY CURING AGENTS AND EPOXY RESIN COMPOSITIONS CONTAINING THE SAME

This Application is a § 371 national stage of PCT International Application No. PCT/EP2019/058033, filed Mar. 29, 2019, which claims the benefit of U.S. Application No. 62/650,376, filed Mar. 30, 2018, the contents of which are hereby incorporated by reference in its entirety into this application.

BACKGROUND OF THE INVENTION

The Mannich reaction is based on the reaction of an aldehyde, generally formaldehyde, a phenolic compound and an amine. Various forms of phenolic compounds, amines and aldehydes have been utilized in this reaction. The Mannich base products are particularly suitable for curing epoxy resins.

Phenalkamine curing agents are a class of Mannich bases obtained by reacting cardanol, an extract of cashew nutshell liquid, an aldehyde compound, such as formaldehyde, and an amine. Generally, they are produced from the reaction of one molar equivalent of cardanol with one to two molar equivalent of an aliphatic polyethylene polyamine and one to two molar equivalent of formaldehyde at 80-100° C. Sometimes aromatic polyamines have also been used for this reaction. The commercially available phenalkamines NC 541 and NC 540 available from Cardolite Inc. use ethylenediamine and diethylenetriamine as the amine sources. The Sunmide 1151 phenalkamine available from Evonik Corp. utilizes m-xylenediamine as the amine raw material.

Phenalkamines are good epoxy resin hardeners for room temperature or low temperature curing applications. In addition, they offer good chemical resistance, excellent water resistance, good compatibility with epoxy resins, low toxicity and good flexibility. As a result, they are used in marine, industrial maintenance and civil engineering applications.

GB Patent No. 1,529,740 describes phenalkamines as mixtures of poly(aminoakylene) substituted phenols (structure according to formula (I) below) prepared from cardanol with polyethylene polyamines and formaldehyde. In general, it is not possible to easily control the molecular weight distribution of these products and hence they are usually viscous liquids.

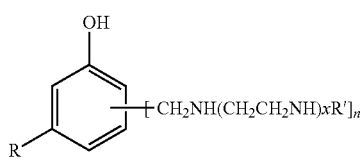

R=hydrocarbyl substituent with 15 carbon atoms, x=1-5, n=1-3, R'=H

U.S. Pat. No. 6,262,148 B1 describes compositions of phenalkamines bearing aromatic or alicyclic rings. These compositions were prepared from cardanol with aldehydes and alicylic or aromatic polyamines. International Application Publication No. WO 2009/080209 A1 describes the preparation of epoxy curing agents comprising phenalkamines blended with polyamine salts. These curing agents were used to enhance the rate of cure of epoxy resins.

There is a need in the art for phenalkamine curing agents for epoxy resins which can accelerate the cure speed at sub-ambient temperature (e.g. 5° C.) and which can be used with minimal amount of volatile organic solvents. Consequently, liquid phenalkamines of low viscosity are highly desirable.

BRIEF SUMMARY OF THE INVENTION

The present disclosure discloses a new structural class of phenalkamines, curing agent compositions comprising such phenalkamines, methods of making such phenalkamines, and methods of making such compositions. These phenalkamines and curing-agent compositions may be used to cure, harden, and/or crosslink an epoxy resin. This invention solves problems associated with phenalkamines and curing agents comprising phenalkamines by providing curing agents which are of low viscosity (<3000 cP at 25° C.) which can be used neat or dissolved in a minimum amount (<20 wt %) of an organic solvent or diluent to effect cure of epoxy resins. In addition, this inventive phenalkamine curing agent can provide dry cure of epoxy coatings at ambient temperature (25° C.) in <8 h or at 5° C. in <16 h.

The present invention relates to a phenalkamine composition obtained by reacting cardanol (structure according to formula (II) below) with the compound triaminononane (structure according to formula (II) below) and an aldehyde to obtain the composition represented by the structure according to formula (IV) below.

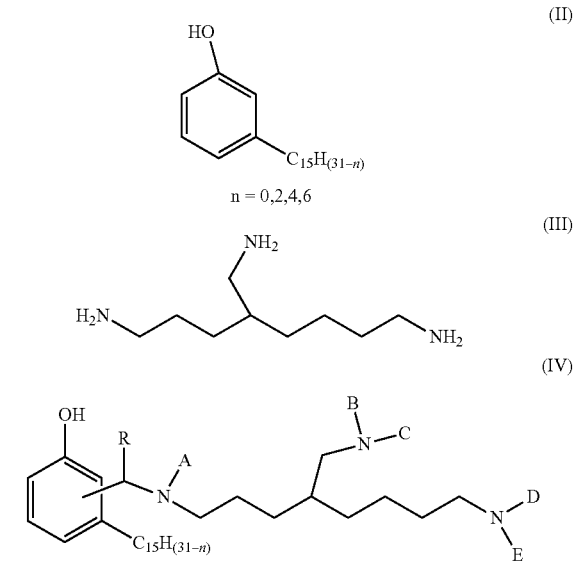

wherein n=0, 2, 4 or 6; wherein R=H, $C_1$-$C_{10}$ alkyl, Ph, or a $C_5$-$C_6$ cycloaliphatic group; and wherein each of A, B, C, D and E=H or

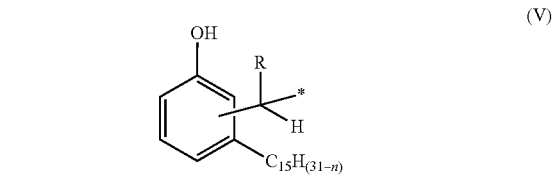

wherein n=0, 2, 4 or 6; wherein, independently, R=H, $C_1$-$C_{10}$ alkyl, Ph, or a $C_5$-$C_6$ cycloaliphatic group, provided that at least two substituents selected from A, B, C, D, and E are H, and bonding occurs via the asterisk.

The present disclosure also provides for a curing agent composition comprising the phenalkamine of formula (IV).

Preferable curing agent compositions of the present disclosure have an amine hydrogen equivalent weight (AHEW) based on 100% solids from about 30 to about 500. The present disclosure, in another aspect, provides amine-epoxy compositions and the cured products produced therefrom. For example, an amine-epoxy composition, in accordance with the present disclosure, comprises a curing agent composition containing the novel phenalkamine composition comprising at least one cardanol group and having at least two active amine hydrogen atoms and an epoxy composition comprising at least one multifunctional epoxy resin.

The present disclosure also provides for the use of a curing agent composition comprising the phenalkamine of formula (IV) as a hardener for epoxy resins.

Articles of manufacture produced from amine-epoxy compositions disclosed herein include, but are not limited to, adhesives, coatings, primers, sealants, curing compounds, construction products, flooring products, and composite products. Further, such coatings, primers, sealants, or curing compounds may be applied to metal or cementitious substrates. The mix of curing agent and epoxy resin often requires no "ripening time" for obtaining contact products with high gloss and clarity. Ripening time or incubation time or induction time is defined as the time between mixing epoxy resin with amine and applying the product onto the target substrate. It could also be defined as the time required for the mix to become clear. Furthermore, the novel phenalkamine compositions also provide faster amine-epoxy reaction rate, and relatively low viscosity. These unique properties provide the advantages of lower tendency to carbamate, shorter time for coatings to dry, and reduced or eliminated amount of solvent needed.

DETAILED DESCRIPTION OF INVENTION

The novel phenalkamine of the present invention can be prepared by reacting cardanol with an aldehyde compound and triaminononane to produce the composition shown in the structure below:

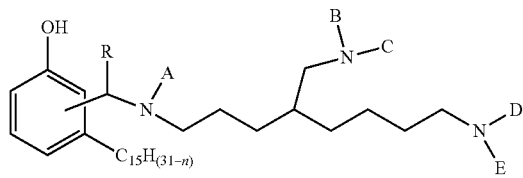

(IV)

wherein n=0, 2, 4 or 6; wherein R=H, $C_1$-$C_{10}$ alkyl, Ph, or a $C_5$-$C_6$ cycloaliphatic group; and wherein each of A, B, C, D and E=H or

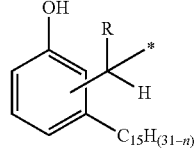

(V)

wherein n=0, 2, 4 or 6; wherein, independently, R=H, $C_1$-$C_{10}$ alkyl, Ph, or a $C_5$-$C_6$ cycloaliphatic group, provided that at least two substituents selected from A, B, C, D, and E are H, and bonding occurs via the asterisk. The person skilled in the art knows that compounds with at least two H can be prepared by selecting adequate mole ratios of cardanol, aldehyde and triaminononane. Preferable alkyl groups include methyl, ethyl, propyl, butyl. Preferable cycloaliphatic groups include, cyclopentyl and cyclohexyl.

Preferably, the mole ratio of cardanol to triaminononane is within the range of from 1:1 to 1:3. In another preferable embodiment, the mole ratio of cardanol to triaminononane is within the range of from 1:1 to 12. Preferably, the mole ratio of triaminononane to aldehyde is within the range of from 1:1 to 1:6. In another preferable embodiment, the mole ratio of triaminononane to aldehyde is within the range of from 1:1 to 1:1.2.

The reaction is preferably carried out in a one-step process by mixing the cardanol with the amine and treating this mixture with formaldehyde at the desired reaction temperature. Alternately, the cardanol may preferably be mixed with the aldehyde and treated with the triaminononane at the reaction temperature. The reaction is preferably carried out at 40° C.-150° C. In another preferable embodiment, the reaction may be carried out at 80° C.-120° C. The product is generally obtained by distillation of water after the reaction is completed.

The aldehyde compound used is represented by the structural formula RCOH. R=H, $C_1$-$C_{10}$ alkyl, Ph, $C_5$-$C_6$ cycloaliphatic group or mixtures thereof. Preferable aldehydes are formaldehyde, acetaldehyde, propionaldehyde, butyraldehyde, pentanal, hexanal, octanal, heptanal, decanal, benzaldehyde, cyclopentanecarboxldehyde, cyclohexnecarboxldehyde. More preferred aldehydes are formaldehyde and acetaldehyde. Formaldehyde can be used as an aqueous solution or n the polymeric form, paraformaldehyde.

The mole ratio of cardanol to triaminononane and the aldehyde determines the extent of the reaction of the three ambo substituents in triaminononane. The three amino groups of triaminononane are of similar reactivity towards substitution on cardanol. Hence mixtures of monoamino, diamino and triamino substituents are expected. The ratio of diamino and triamino substituent on cardanol increases when the molar ratio of amino groups to cardanol is >1.0 assuming an equivalent molar ratio of amino groups to aldehyde. The number of amine groups that are substituted on cardanol affects the viscosity of the composition obtained. The product viscosity is preferably in the range from 300 centipoise to 3,000 centipoise at 25° C. In another preferred embodiment, the product viscosity is in the range from 300 centipoise to 1500 centipoise at 25° C. In yet another embodiment, the preferred product viscosity is in the range from 300 centipoise to 1,000 centipoise at 25° C. This low viscosity is advantageous for using this curing agent in the preparation of epoxy coatings since it requires none or a minimal amount of volatile organic solvent which may be beneficial for the environment and for the health and safety of workers using this material.

The present disclosure also provides for a curing agent composition comprising the phenalkamine of formula (IV).

The present disclosure also provides amine-epoxy compositions and the cured products produced therefrom. The latter comprise the reaction product of:

(a) a curing agent composition comprising the triaminononane derived Mannich base of cardanol (phenalkamine) shown below:

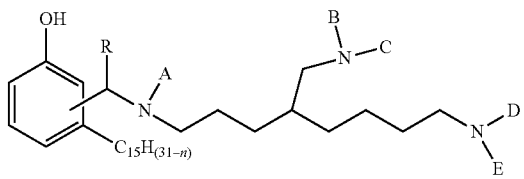

(IV)

wherein n=0, 2, 4 or 6; wherein R=H, $C_1$-$C_{10}$ alkyl, Ph, or a $C_5$-$C_6$ cycloaliphatic group; and wherein each of A, B, C, D and E=H or

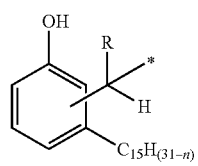

(V)

wherein n=0, 2, 4 or 6; wherein, independently, R=H, $C_1$-$C_{10}$ alkyl, Ph, or a $C_5$-$C_6$ cycloaliphatic group, provided that at least two substituents selected from A, B, C, D, and E are H, and bonding occurs via the asterisk; and
(b) an epoxy composition comprising at least one multifunctional epoxy resin.

The present disclosure also provides for the use of a curing agent composition comprising the phenalkamine of formula (IV) as a hardener for epoxy resins.

The present disclosure also includes articles of manufacture produced from an amine-epoxy composition as described above. Such articles preferably include an adhesive, a coating, a primer, a sealant, a curing compound, a construction product, a flooring product, a composite product, laminate, potting compounds, grouts, fillers, cementitious grouts, or self-leveling flooring. Additional components or additives may be used together with the compostions of the present disclosure to produce articles of manufacture. Further, such coatings, primers, sealants, curing compounds or grouts may be applied to metal or cementitious substrates.

The relative amount chosen for the epoxy composition versus that of the curing agent composition, may vary depending upon, for example, the end-use article, its desired properties, and the fabrication method and conditions used to produce the end-use article. For instance, in coating applications using certain amine-epoxy compostions, incorporating more epoxy resin relative to the amount of the curing agent composition may result in coatings which have increased drying time, but with increased hardness and improved appearance as measured by gloss. Amine-epoxy compositions of the present disclosure preferably have stoichiometric ratios of epoxy groups in the epoxy composition to amine hydrogens in the curing agent composition ranging from 1.5:1 to 0.7:1. For example, such amine-epoxy compostions may preferably have stoichiometric ratios of 1.5:1, 1.4:1, 1.3:1, 1.2:1, 1.1:1, 1:1, 0.9:1, 0.8:1, or 0.7:1. In another aspect, the stoichiometric ratio preferably ranges from 1.3:1 to 0.7:1, or from 1.2:1 to 0.8:1, or from 1.1:1 to 0.9:1.

Amine-epoxy compositions of the present disclosure comprise a curing agent composition and an epoxy composition comprising at least one multifunctional epoxy resin. Multifunctional epoxy resin, as used herein, describes compounds containing 2 or more 1,2-epoxy groups per molecule. The epoxy resin is preferably selected from the group consisting of aromatic epoxy resin, alicyclic epoxy resin, aliphatic epoxy resin, glycidyl ester resin, thioglycidyl ether resin, N-glycidyl ether resin, and combinations thereof.

Preferable aromatic epoxy resins suitable for use in the present disclosure comprise the glycidyl ethers of polyhydric phenols, including the glycidyl ethers of dihydric phenols. Further preferred are the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Additionally, advanced dihydric phenols of the following structure also are useful in the present disclosure:

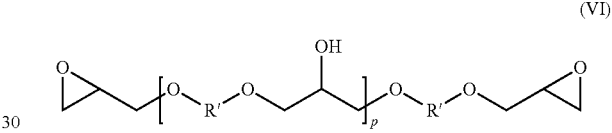

(VI)

wherein R' is a divalent hydrocarbon radical of a dihydric phenol, such as those dihydric phenols listed above, and p is an average value between 0 and 7. Materials according to this formula may be prepared by polymerizing mixtures of a dihydric phenol and epichlorohydrin, or by advancing a mixture of a diglycidyl ether of the dihydric phenol and the dihydric phenol. While in any given molecule the value of p is an integer, the materials are invariably mixtures which may be characterized by an average value of p which is not necessarily a whole number. Polymeric materials with an average value of p between 0 and 7 may be used in one aspect of the present disclosure.

In one aspect of the present disclosure, the at least one multifunctional epoxy resin is preferably a diglycidyl ether of bisphenol-A (DGEBA), an advanced or higher molecular weight version of DGEBA, a diglycidyl ether of bisphenol-F, a diglycidyl ether of novolac resin, or any combination thereof. Higher molecular weight versions or derivatives of DGEBA are prepared by the advancement process, where excess DGEBA is reacted with bisphenol-A to yield epoxy terminated products. The epoxy equivalent weights (EEW) for such products range from 450 to 3000 or more. Because these products are solid at room temperature, they are often referred to as solid epoxy resins.

In preferred embodiments, the at least one multifunctional epoxy resin is the diglycidyl ether of bisphenol-F or bisphenol-A represented by the following structure:

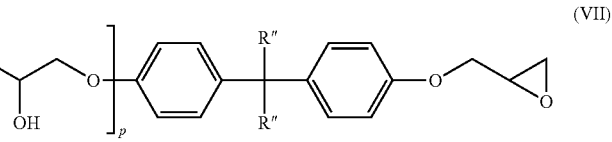

(VII)

wherein R'=H or CH$_3$, and p is an average value between 0 and 7. DGEBA is represented by the above structure when R'=CH$_3$ and p=0. DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of about 174. Resins with EEWs between about 250 and about 450, also prepared by the advancement process, are referred to as semi-solid epoxy resins because they are a mixture of solid and liquid at room temperature. Multifunctional resins with EEWs based on solids of about 160 to about 750 are useful in the present disclosure. In another aspect the multifunctional epoxy resin has an EEW in a range from about 170 to about 250.

Examples of alicyclic epoxy compounds include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethyl hexyl epoxyhexahydrophthalate.

Examples of aliphatic epoxy compounds include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to, glycidyl ethers of polyols, such as 1,4-butanediol diglycidyl ether; 1,6-hexanediol diglycidyl ether; a triglycidyl ether of glycerin; a triglycidyl ether of trimethylol propane; a tetraglycidyl ether of sorbitol; a hexaglycidyl ether of dipentaerythritol; a diglycidyl ether of polyethylene glycol; and a diglycidyl ether of polypropylene glycol; polyglycidyl ethers of polyether polyols obtained by adding one type, or two or more types, of alkylene oxide to aliphatic polyols, such as ethylene glycol, propylene glycol, trimethylol propane, and glycerin.

Glycidyl ester resins are obtained by reacting a polycarboxylic acid compound having at least two carboxyl acid groups in the molecule and epichlorohydrin. Examples of such polycarboxylic acids include aliphatic, cycloaliphatic, and aromatic polycarboxylic acids. Examples of aliphatic polycarboxylic acids include oxalic acid, succinic acid, glutaric acid, adipic acid, pimelic acid, sebacic acid, suberic acid, azelaic acid, or dimerised or trimerised linoleic acid. Cycloaliphatic polycarboxylic acids include tetrahydrophthalic acid, 4-methyltetrahydrophthalic acid, hexahydrophthalic acid or 4-methylhexahydrophthalic acid. And aromatic polycarboxylic acids include phthalic acid, isophthalic acid or terephthalic acid.

Thioglycidyl ether resins are derived from dithiols, for example, ethane-1,2-dithiol or bis(4-mercaptomethylphenyl) ether.

N-glycidyl resins are obtained by dehydrochlorination of the reaction products of epichlorohydrin with amines containing at least two amine hydrogen atoms. Such amines are, for example, aniline, n-butylamine, bis(4-aminophenyl) methane, m-xylylenediamine or bis(4-methylaminophenyl) methane. The N-glycidyl resins also include, however, triglycidyl isocyanurate, N,N'-diglycidyl derivatives of cycloalkylene ureas, e.g., ethylene urea or 1,3-propylene urea, and diglycidyl derivatives of hydantoins, e.g., 5,5-dimethylhydantoin.

For one or more of the embodiments, the resin component further includes a reactive diluent. Reactive diluents are compounds that participate in a chemical reaction with the hardener component during the curing process and become incorporated into the cured composition, and are preferably monofunctional epoxides. Reactive diluents may also be used to vary the viscosity and/or cure properties of the curable compositions for various applications. For some applications, reactive diluents may impart a lower viscosity to influence flow properties, extend pot life and/or improve adhesion properties of the curable compositions. For example, the viscosity may be reduced to allow an increase in the level of pigment in a formulation or composition while still permitting easy application, or to allow the use of a higher molecular weight epoxy resin. Thus, it is within the scope of the present disclosure for the epoxy component, which comprises at least one multifunctional epoxy resin, to further comprise a monofunctional epoxide. Examples of monoepoxides include, but are not limited to, styrene oxide, cyclohexene oxide and the glycidyl ethers of phenol, cresols, tert-butylphenol, other alkyl phenols, butanol, 2-ethylhexanol, C4 to C14 alcohols, and the like, or combinations thereof. The multifunctional epoxy resin may also be present in a solution or emulsion, with the diluent being water, an organic solvent, or a mixture thereof. The amount of multifunctional epoxy resin may range from 50% to 100%, 50% to 90%, 60% to 90%, 70% to 90%, and in some cases 80% to 90%, by weight, of the epoxy component. For one or more of the embodiments, the reactive diluent is less than 60 weight percent of a total weight of the resin component.

Particularly suitable multifunctional epoxy compounds are the diglycidyl ethers of bisphenol-A and bisphenol-F, the advanced diglycidyl ethers of bisphenol-A and bisphenol-F, and the epoxy novolac resins. The epoxy resin may be a single resin, or K may be a mixture of mutually compatible epoxy resins.

Compositions of the present disclosure may be used to produce various articles of manufacture. Depending on the requirements during the manufacturing of or for the end-use application of the article, various additives may be employed in the formulations and compostions to tailor specific properties. These additives include, but are not lined to, solvents (including water), accelerators, plasticizers, fillers, fibers, such as glass or carbon fibers, pigments, pigment dispersing agents, rheology modifiers, thixotropes, flow or leveling aids, surfactants, defoamers, biocides, or any combination thereof. It is understood that other mixtures or materials that are known in the art may be included in the compostions or formulations and are within the scope of the present disclosure.

The present disclosure also is directed to articles of manufacture manufactured using the compositions disclosed herein. For example, an article may be produced from an amine-epoxy composition which comprises a curing agent composition and an epoxy composition. The curing agent composition may comprise the triaminononane derived Mannich base of cardanol (phenalkamine). The epoxy composition may comprise at least one multifunctional epoxy resin. Optionally, various additives may be present in the compositions or formulations used to produce fabricated articles, dependent upon the desired properties. These additives may include, but are not limited to, solvents (including water), accelerators, plasticizers, fillers, fibers, such as glass or carbon fibers, pigments, pigment dispersing agents, rheology modifiers, thixotropes, flow or leveling aids, surfactants, defoamers, biocides, or any combination thereof.

Articles in accordance with the present disclosure include, but are not limited to, a coating, an adhesive, a construction product, a flooring product, or a composite product. Coatings based on these amine-epoxy compositions may be solvent-free or may contain diluents, such as water or organic solvents, as needed for the particular application. Coatings may contain various types and levels of pigments for use in paint and primer applications. Amine-epoxy coating compositions comprise a layer having a thickness ranging from 40 to 400 μm (micrometer), preferably 80 to 300 μm, more preferably 100 to 250 μm, for use in a protective coating applied onto metal substrates. In addition, for use in a flooring product or a construction product, coating compositions comprise a layer having a thickness ranging from 50 to 10,000 μm, depending on the type of product and the required end-properties. A coating product that delivers limited mechanical and chemical resistances comprises a layer having a thickness ranging from 50 to 500 μm, preferably 100 to 300 μm; whereas a coating product, such as, for example, a self-leveling floor that delivers high mechanical and chemical resistances comprises a layer having a thickness ranging from 1,000 to 10,000 μm, preferably 1,500 to 5,000 μm.

Various substrates are suitable for the application of coatings of this invention with proper surface preparation, as is well known to one of ordinary skill in the art. Such substrates include, but are not limited to, concrete and various types of metals and alloys, such as steel and aluminium. Coatings of the present disclosure are suitable for the painting or coating of large metal objects or cementitious substrates including ships, bridges, industrial plants and equipment, and floors.

Coatings of this invention may be applied by any number of techniques including spray, brush, roller, paint mitt, and the like. In order to apply very high solids content or 100% solids coatings of this invention, plural component spray application equipment may be used, in which the amine and epoxy components are mixed in the lines leading to the spray gun, in the spray gun itself, or by mixing the two components together as they leave the spray gun. Using this technique may alleviate limitations with regard to the pot life of the formulation, which typically decreases as both the amine reactivity and the solids content increases. Heated plural component equipment may be employed to reduce the viscosity of the components, thereby improving ease of application.

Construction and flooring applications include compositions comprising the amine-epoxy compositions of the present disclosure in combination with concrete or other materials commonly used in the construction industry. Applications of compositions of the present disclosure include, but are not lied to, its use as a primer, a deep penetrating primer, a coating, a curing compound, and/or a sealant for new or old concrete, such as referenced in ASTM C309-97, which is incorporated herein by reference. As a primer or a sealant, the amine-epoxy compositions of the present disclosure may be applied to surfaces to improve adhesive bonding prior to the application of a coating. As it pertains to concrete and cementitious application, a coating is an agent used for application on a surface to create a protective or decorative layer or a coat. Crack injection and crack filling products also may be prepared from the compositions disclosed herein. Amine-epoxy compostions of the present disclosure may be mixed with cementitious materials, such as concrete mix, to form polymer or modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

In a particular use of the curing agent composition of the present disclosure, coatings may be applied to various substrates, such as concrete and metal surfaces at low temperature, with fast cure speed and good coating appearance. This is especially important for top-coat application where good aesthetics is desired, and provides a solution to a long-standing challenge in the industry where fast low-temperature cure with good coating appearance remains to be overcome. With fast low-temperature cure speed, the time service or equipment is down may be shortened, or for outdoor applications, the work season may be extended in cold climates.

Fast epoxy curing agents enable amine-cured epoxy coatings to cure in a short period of time with a high degree of cure. The cure speed of a coating is monitored by thin film set time (TFST) which measures the time period a coating dries. The thin film set time is categorized in 4 stages: phase 1, set to touch; phase 2, tack free: phase 3, dry hard; and phase 4, dry through. The phase 3 dry time is indicative of how fast a coating cures and dries. For a fast ambient cure coating, phase 3 dry time is less than 6 hours, or less than 4 hours, or preferred to be less than 4 hours. Low temperature cure typically refers to cure temperature below ambient temperature, 10° C. or 5° C., or 0° C. In some cases. For a fast low temperature cure, phase 3 dry time at 5° C. is less than 16 hours, with a significant productivity benefit being provided for values where phase 3 dry times are less than 10 hours and preferably less than 8 hours.

How well a coating cures is measured by the degree of cure. Degree of cure is often determined by using DSC (differential scanning calorimetry) technique which is well-known to those skilled in the art. A coating that cures thoroughly will have a degree of cure at ambient temperature (25° C.) of at least 85%, or at least 90%, or at least 95% after 7 days. A coating that cures thoroughly will have a degree of cure at 5° C. of at least 80%, or at least 85%, or at least 90% after 7 days.

Many of the fast low temperature epoxy curing agents may cure an epoxy resin fast. However due to poor compatibility of the epoxy resin and curing agents especially at low temperature of 10 degrees Celsius or 5 degrees Celsius, there is phase separation between resin and curing agent and curing agent migrating to coating surface, resulting in poor coating appearance manifested as sticky and cloudy coatings. Good compatibility between epoxy resin and curing agent leads to clear glossy coating with good carbamation resistance and good coating appearance. The curing agent compositions of the present disclosure offers the combination of fast cure speed, good compatibility and high degree of cure.

In another aspect of this invention the phenalkamine curing agent of this invention may be used in combination with another amine curing agent (as a co-curing agent) for curing epoxy resins.

Hence, the amine-epoxy composition, in accordance with the present disclosure, comprises: (a) a curing agent composition comprising the triaminononane derived Mannich base of cardanol (phenalkamine) shown below:

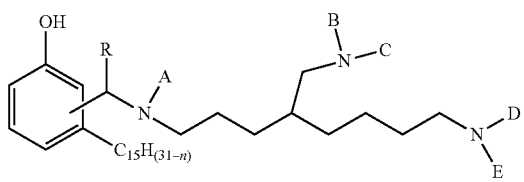

(IV)

wherein n=0, 2, 4 or 6; wherein R=H, $C_1$-$C_1$ alkyl, Ph, or a $C_5$-$C_6$ cycloaliphatic group; and wherein each of A, B, C, D and E=H or

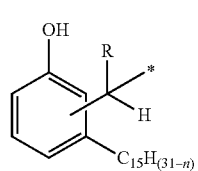

(V)

wherein n=0, 2, 4 or 6; wherein, independently, R=H, $C_1$-$C_{10}$ alkyl, Ph, or a $C_5$-$C_6$ cycloaliphatic group, provided that at least two substituents selected from A, B, C, D, and E are H, and bonding occurs via the asterisk;
(b) an epoxy composition comprising at least one multifunctional epoxy resin as described above; and
(c) an amine co-curing agent having at least two amine functionalities.

Preferable examples of amine co-curing agents include diethylenetriamine (DETA), triethylenetetramine (TETA), tetraethylenepentamine (TEPA), pentaethylenehexamine (PEHA), hexmethylenediamine (HMDA), 1,3-pentanediamine (DYTEK™ EP), 2-methyl-1,5-pentanediamine (DYTEK™A) N-(2-aminoethyl)-1, 3-propanediamine (N-3-Amine), N,N'-1, 2-ethanediylbis-1, 3-propanediamine (N4-amine), or dipropylenetriamine; an arylaliphatic amine such as m-xylylenediamine (mXDA), or p-xylylenediamine; a cycloaliphatic amine such as 1,3-bisaminocyclohexylamine (1,3-BAC), isophorone diamine (IPDA), or 4,4'-methylenebiscyclohexanamine; an aromatic amine such as m-phenylenediamine, diaminodiphenylmethane (DDM), or diaminodiphenylsulfone (DDS); a heterocyclic amine such as N-aminoethylpiperazine (NAEP), or 3,9-bis(3-aminopropyl)2, 4,8, 10-tetraoxaspiro (5,5)undecane; a polyalkoxypolyamine where the alkoxy group can be an oxyethylene, oxypropylene, oxy-1, 2-butylene, oxy-1, 4-butylene or co-polymers thereof such as 4,7-dioxadecane-1, 10-diamine, I-propanamine, 3,3'-(oxybis (2, 1-ethanediyloxy))bis(di-aminopropylated diethylene glycol ANCAMINE1922A), poly(oxy(methyl-1, 2-ethanediyl)), alpha-(2-aminomethyl-ethyl)omega-(2-aminomethylethoxy) (JEFFAMINE D 230, D-400), triethyleneglycoldiamine and oligomers (JEFFAMINEXTJ-504, JEFFAMINE XTJ-512), poly(oxy(methyl-1, 2-ethanediyl)), alpha, alpha'-(oxydi-2, 1-ethanediyl)bis (omega-(aminomethylethoxy)) (JEFFAMINE XTJ-511), bis (3-aminopropyl)polytetrahydrofuran 350, bis(3-aminopropyl)polytetrahydrofuran 750, poly(oxy(methyl-1, 2-ethanediyl)), a-hydro-w-(2-aminomethylethoxy)ether with 2-ethyl-2-(hydroxymethyl)-1, 3-propanediol (3:I) (JEFFAMINE T-403), and diaminopropyldiaminopropyl dipropylene glycol.

Other amine co-curing agents include amidoamine and polyamide curing agents. Polyamide curing agents are comprised of the reaction products of dimerized fatty acid (diner acid) and polyethyleneamines, and usually a certain amount of monomeric fatty acid which helps to control molecular weight and viscosity. "Dimerized" or "dimer" or "polymerized" fatty acid refers to polymerized acids obtained from unsaturated fatty acids. They are described more fully in T. E. Breuer, 'Dimer Acids', in J. I. Kroschwitz (ed.), Kirk-Othmer Encyclopedia of Chemical Technology, 4' Ed., Wiley, N.Y. 1993, Vol. 8, pp. 223-237. Common monofunctional unsaturated C-6 to C-20 fatty acids also employed in making polyamides include tall oil fatty acid (TOFA) or soya fatty acid or the like.

Other amine co-curing agents include phenalkamines and Mannich bases of phenolic compounds with amines and formaldehyde.

The weight ratio of triaminononane derived Mannich base of cardanol (phenalkamine) and amine co-curing agent is preferably 1:1 to 1:0.05. In another preferred embodiment, the weight ratio of triaminononane derived Mannich base of cardanol (phenalkamine) and amine co-curing agent is 1:0.75 to 1:0.25.

The combined triaminononane derived Mannich base of cardanol (phenalkamine) and amine co-curing agent epoxy compositions of the present disclosure preferably have stoichiometric ratios of epoxy groups in the epoxy composition to amine hydrogens in the curing agent composition ranging from 1.5:1 to 0.7:1. For example, such amine-epoxy compositions may preferably have stoichiometric ratios of 1.5:1, 1.4:1, 1.3:1, 1.2:1, 1.1:1, 1:1, 0.9:1, 0.8:1, or 0.7:1. In another preferably aspect, the stoichiometric ratio ranges from 1.3:1 to 0.7:1, or from 1.2:1 to 0.8:1, or from 1.1:1 to 0.9:1.

The following invention is directed to the following aspects:
<1> A phenalkamine represented by the structure of formula (IV):

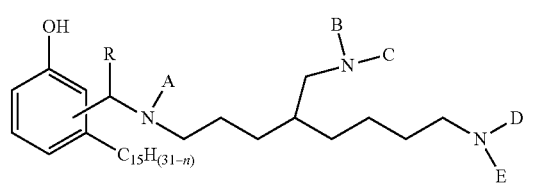

(IV)

wherein n=0, 2, 4 or 6; wherein R=H, $C_1$-$C_{10}$ alkyl, Ph, or a $C_5$-$C_6$ cycloaliphatic group; and wherein each of A, B, C, D and E=H or a group with the structure of formula (V)

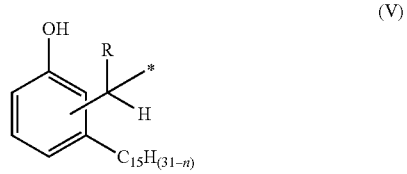

wherein n=0, 2, 4 or 6, wherein, independently, R=H, $C_1$-$C_{10}$ alkyl, Ph, or a $C_5$-$C_6$ cycloaliphatic group and bonding occurs via the asterisk.

<2> A preferred curing agent composition comprising the phenalkamine according to aspect <1>.

<3> A preferred curing agent composition of aspect <2> further comprising an additional amine having at least two amine functionalities.

<4> Use of a phenalkamine according to aspect <1> or of a curing agent composition according to aspect <2> or <3> as hardener for epoxy resins.

<5> A preferred use of aspect <4>, wherein the epoxy resins comprise at least one multifunctional epoxy resin.

<6> A preferred use of aspect <4>, wherein the epoxy resins are selected from the group consisting of aromatic epoxy resins, alicyclic epoxy resins, aliphatic epoxy resins, glycidyl ester resins, thioglycidyl ether resins, N-glycidyl ether resins, and combinations thereof.

<7> A preferred use of aspect <6>, wherein the epoxy resins comprise a glycidyl ether of polyhydric phenol.

<8> A preferred use of aspect <6>, wherein the epoxy resins comprise at least one glycidyl ether selected from the group of glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane, bis-(4-hydroxyphenyl)-methane, novolac resins, and combinations thereof.

<9> A preferred use of aspect <6>, wherein the epoxy resins comprise at least one dihydric phenol with the structure of formula (VI):

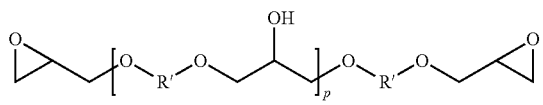

wherein R" is a divalent hydrocarbon radical of a dihydric phenol, and p is an average value between 0 and about 7.

<10> A preferred use of aspect <5>, wherein the at least one multifunctional epoxy resin comprises at least one of the diglycidyl ethers of bisphenol-A, the advanced diglycidyl ethers of bisphenol-A, and the diglycidyl ethers of bisphenol-F.

<11> A preferred use of aspect <10>, wherein the at least one multifunctional epoxy resin is represented the structure of formula (VII):

wherein R' is H or $CH_3$, and p is an average value between 0 and about 7.

<12> A preferred use of aspect <5>, wherein the epoxy resins further comprise a monofunctional epoxide.

<13> A preferred use of aspect <4>, wherein the stoichiometric ratio of epoxy groups in the epoxy composition to amine hydrogens in the curing agent composition ranges from 1.5:1 to 0.7:1.

<14> A method for producing the phenalkamine of aspect <1> comprising the steps of reacting cardanol, triaminononane and an aldehyde.

<15> A preferred method of aspect <14>, wherein the mole ratio of cardanol to triaminononane is within the range of from 1:1 to 1:3 and the mole ratio of triaminononane to aldehyde is within the range of from 1:1 to 1:6.

<16> A preferred method of aspect <14>, wherein the aldehyde is selected from the group consisting of formaldehyde, paraformaldehyde, acetaldehyde, propionaldehyde, butyraldehyde, pentanal, hexanal, octanal, heptanal, decanal, benzaldehyde, cyclopentanecarboxaldehyde, and cyclohexanecarboxldehyde.

<17> A method for producing the curing agent composition of aspect <2> comprising combining a phenalkamine of formula (IV) and an additional amine having at least two amine functionalities.

<18> Use of a phenalkamine according to aspect <1> or of a curing agent composition according to aspect <2> or <3>, together with at least one epoxy resin, for the preparation of hardened articles of manufacture.

<19> A preferred use of aspect <18>, wherein the article is a coating, an adhesive, a construction product, a flooring product, or a composite product.

EXAMPLES

These Examples are provided to demonstrate certain aspects of the invention and shall not limit the scope of the claims appended hereto.

Example 1: Synthesis of the Phenalkamine of Triaminononane with Molar Ratio of Cardanol:Triaminononane:Formaldehyde (1:1:1)

A 3-neck 1 L round bottom flask equipped with $N_2$ inlet, addition funnel and temperature probe was charged with cardanol (298 g, 1.0 mole) and triaminononane (TAN) (173.3 g, 1.0 mole). The mixture was heated to 80° C. A 37% solution of formaldehyde (81 g, 37 wt. %, 30 g, 1.0 mole) was added to maintain a reaction temperature of 80-90° C. After the addition the mixture was kept at 90-95° C. for 1 h. Water was distilled at 120° C. and the product was obtained as a light brown liquid.

Example 2: Synthesis of the Phenalkamine of Triaminononane with Molar Ratio of Cardanol:Triaminononane:Formaldehyde (1:1.3:1.3)

A 3-neck 1 L round bottom flask equipped with $N_2$ inlet, addition funnel and temperature probe was charged with cardanol (298 g, 1.0 mole) and TAN (225.29 g, 1.30 mole). The mixture was heated to 80° C. A 37% solution of formaldehyde (105.40 g, 37 wt. %, 39 g, 1.3 mole) was

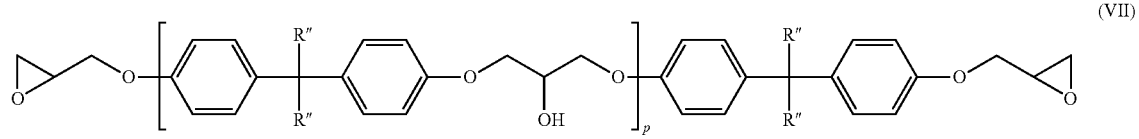

added to maintain a reaction temperature of 80-90° C. After the addition the mixture was kept at 90-95° C. for 1 h. Water was distilled at 120° C. and the product was obtained as a light brown liquid.

Examples 1A-3B

Curing agent mixtures were prepared by mixing the components given in the above examples. with the epoxy component of standard bisphenol-A based epoxy resin of (Epon 828, DER 331 type), EEW 190, unless specified otherwise. The formulations used are defined in Table 1. They were then mixed employing a stoichiometric level of 1:1 (amine:epoxy equivalents). The curing agents were tested neat and at 80% solids in a combination of xylene: n-butanol (3:1 by weight). Comparative Example (3) is a commercially available Phenalkamine Curing Agent Derived from Ethylenediamine [EDA] and was Used as a Reference.

TABLE 1

Clear Coat Formulation Screening - TAN Phenalkamines

| Property | | Ex 1A | Ex 2A | Ex 3A | Ex 1B | Ex 2B | Ex 3B |
|---|---|---|---|---|---|---|---|
| | | Solvent free | | | Solvent based | | |
| Liquid BADGE Epoxy resin (EEW 190) | g | 100 | 100 | 100 | 100 | 100 | 100 |
| Curing agent [Ex 1] (AHEW 92) | g | 49 | — | — | 49 | — | — |
| Curing agent [Ex 2] (AHEW 97) | g | — | 51 | — | — | 51 | — |
| Commercial [EDA] phenalkamine [Ex 3] (AHEW 125) | g | — | — | 65.6 | — | — | 65.6 |
| Xylene/n-butanol (3:1 by wt) | g | — | 0 | 0 | 12.3 | 12.7 | 16.4 |
| Total solids | % | 100 | 100 | 100 | 92.3 | 92.2 | 90.9 |
| Total mix | g | 150 | 151 | 165.6 | 161.3 | 163.7 | 182 |

Formulations as defined in Table 1, were subjected to a series of application tests to determine their general performance attributes. The test protocols adapted are defined in Table 2.

TABLE 2

Test Methods

| Property | Response | Test Method |
|---|---|---|
| Gel time | 150 g sample | D2471 |
| Drying time: Beck-Koller (BK) recorder | Thin film set times phases 2 & 3 (hour) | ASTM D5895 |
| Specular gloss | Gloss at 60° | ASTM D523 |
| Persoz pendulum hardness | Persoz hardness (s) | ASTM D4366 |
| Degree of cure (DSC) | Based on residual exotherm via DSC 1-7 day cure | Internal |
| Carbamation Resistance | Whitening of film after exposure to high humidity @ 23° C. & 5° C. | Internal |

The gel time characterizes the time composition transitions from a liquid to a gel. The gel time of the amine-epoxy compositions was measured with a TECHNE gelation timer model FGT 6 using ASTM D2471. The dry time or thin film set time (TFS) was determined using a Beck-Koller recorder, in accordance with ASTM D5895. The amine-epoxy coatings were prepared on standard glass panels at a wet film thickness of 150μ WFT (wet film thickness) using a Bird applicator resulting in dry film thicknesses from 100-130μ. The coatings were cured at 23° C. and 5° C. and 60% relative humidity (RH). The data for curing agents without (series A) and with 20% solvent (series B) are reported in Table 3.

TABLE 3

Performance Properties of TAN-amine Phenalkamine Curing Agent

| Property | Ex 1A | Ex 2A | Ex 3A | Ex 1B | Ex 2B | Ex 3B |
|---|---|---|---|---|---|---|
| Gel time (min.) | 83 | 64 | 55 | Nd | nd | nd |
| Tg (° C.) | 52 | 52 | 55 | Nd | nd | nd |

TABLE 3-continued

Performance Properties of TAN-amine Phenalkamine Curing Agent

| Property | | | Ex 1A | Ex 2A | Ex 3A | Ex 1B | Ex 2B | Ex 3B |
|---|---|---|---|---|---|---|---|---|
| BK- TFST | Ph 2 | | 2:30 | 2:30 | 3:45 | 4:30 | 4:00 | 8:30 |
| (h) (23° C.) | Ph 3 | | 3:00 | 4:15 | 7:30 | 5:30 | 5:00 | 11:30 |
| BK- TFST | Ph 2 | | 7:00 | 8:00 | 8:15 | 9:15 | 9:30 | 12:45 |
| (h) (5° C.) | Ph 3 | | 8:30 | 9:45 | 12:30 | 13:30 | 12:15 | 18:45 |
| Persoz | 24 h | | 162 | 145 | 235 | 90 | 76 | 96 |
| (23° C.) | 7 d | | 293 | 220 | 330 | 185 | 188 | 215 |
| Coating appearance (23° C.) | | | Clear, pale amber | Clear, pale amber | Clear dark amber | Clear, pale amber | Clear, pale amber | Clear dark amber |
| Gloss (23° C.) Specular 60° | 1 d | | 134 | — | 72 | 132 | — | 138 |
| Coating appearance (5° C.) | 1 d | | Sl Haze | Sl Haze | Hazy film Greasy | Sl Haze | Sl Haze | Sl Haze |
| Gloss (5° C.) Specular 60° | 1 d | | 108 | — | 70 | 88 | — | 86 |
| Carbamation Resistance (23° C.) | 1 d/7 d | | 3/3 | 3/3 | 3/3 | 3/3 | 3/3 | 3/3 |
| Carbamation Resistance (5° C.) | 1 d/7 d | | 2/3 | 2/3 | 2/3 | 2/2 | 2/2 | 2/2 |
| Degree of cure (%) (25° C.) | 24 h | | 79 | nd | 66 | nd | nd | nd |

The coatings containing the curing agent of the present invention exhibit much faster thin film dry times compared to the dry speeds obtained using the commercially available EDA based phenalkamine when cured at both 23° C. and 5° C. This is deemed a significant performance benefit for these type of coatings as the faster property development can provide productivity benefits in industrial coating applications. The presence of solvent in the coating systems, while enabling lower application viscosities, in all cases resulted in a decrease in the overall dry speed. Despite this, the dry speed properties of the curing agents based on this invention are faster than those based on the commercial EDA based offering.

At 23° C. all coatings showed good gloss development and were free from any greasy amine and surface defects. At lower application temperatures all coatings, including the reference phenalkamine showed a decrease in the gloss and the clear coats developed an inherent haze. The gloss reduction for the new phenalkamine based on TAN-amine were lower vs the EDA based material, which indicates improved compatibility for the curing agent technology based on the TAN amine. Comparable surface appearance was observed when curing agents were formulated with compatibilzing solvents. The results obtained clearly show that the coatings containing the curing agent of the present invention possess both fast cure and good coating appearance, indicative of good compatibility between curing agent and epoxy resin.

Many amine based systems are prone to carbamation, this is where free amine present on the surface of a coating reacts with moisture and carbon dioxide in the atmosphere and the result is the formation of an insoluble white salt on the coating surface. In order to assess this, clear coatings were applied to clean Lenata chart at a wet film thickness of about 75μ (wet film thickness) using a Bird applicator. Lenata chart was cleaned with ethanol before use. The coatings were cured at 23° C. and 5° C. and 60% relative humidity (RH) for 1 day, 2 days, and 7 days. A lint free cotton patch was placed on the test panel, ensuring that it is at least 12 mm from the edge of the panel. The cotton patch was dampened with 2-3 ml of de-mineralized water and covered with a suitable lid (e.g. watch glass). The panel was left undisturbed for the specified time (standard times is 24 h). After that time, the patch was removed and the coating was dried with a cloth or tissue. The panel was examined immediately for carbamation and rated where 5 represents no carbamation, excellent surface and 0 represents excessive whitening or severe carbamation. The data, as summarized in Table 3, indicates that the coatings cured with the curing agents of the present invention have comparable carbamation resistance especially when applied at low temperature of 5° C. to the standard EDA commercial grade. The new TAN-amine phenalkamine also exhibits a higher initial degree of through cure as measured by DSC, achieving 79% cure vs 66% cure or the EDA grade following 24 hrs application at 25° C.

The invention claimed is:

1. A phenalkamine represented by the structure of formula (IV):

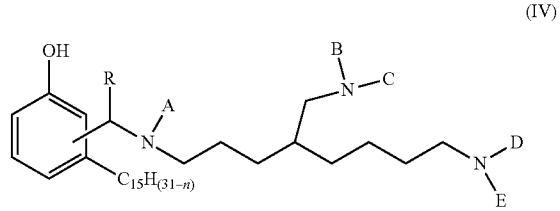

(IV)

wherein n=0, 2, 4 or 6; wherein R=H, $C_1$-$C_{10}$ alkyl, Ph or a $C_5$-$C_6$ cycloaliphatic group;
and wherein each of A, B, C, D and E=H or a group with the structure of formula (V)

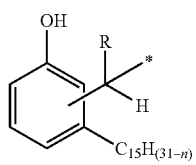

(V)

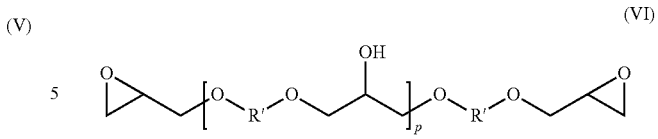

wherein n=0, 2, 4 or 6, wherein, independently, R=H, $C_1$-$C_{10}$ alkyl, Ph, or a $C_5$-$C_6$ cycloaliphatic group, provided that at least two substituents selected from A, B, C, D and E are H, at least one substituent selected from A, B, C, D and E is a group with the structure of formula (V), and bonding occurs via the asterisk.

2. A curing agent composition comprising the phenalkamine according to claim 1.

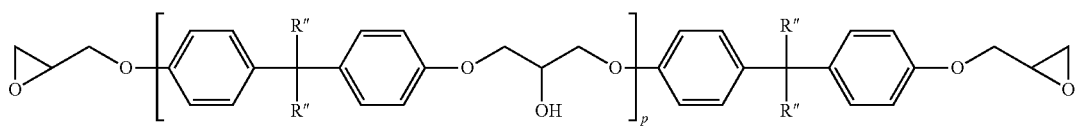

3. The curing agent composition of claim 2 further comprising an additional amine having at least two amine functionalities.

4. An amine-epoxy composition comprising the reaction product of the curing agent composition according to claim 2 and an epoxy component.

5. The amine-epoxy composition of claim 4, wherein the epoxy component comprises at least one multifunctional epoxy resin.

6. The amine-epoxy composition of claim 5, wherein the at least one multifunctional epoxy resin is selected from the group consisting of aromatic epoxy resins, alicyclic epoxy resins, aliphatic epoxy resins, glycidyl ester resins, thioglycidyl ether resins, N-glycidyl ether resins, and combinations thereof.

7. The amine-epoxy composition of claim 6, wherein the at least one multifunctional epoxy resin comprises a glycidyl ether of polyhydric phenol.

8. The amine-epoxy composition of claim 6, wherein the at least one multifunctional epoxy resin comprises at least one glycidyl ether selected from the group of glycidyl ethers of: resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane, bis-(4-hydroxyphenyl)-methane, novolac resins, and combinations thereof.

9. The amine-epoxy composition of claim 6, wherein the at least one multifunctional epoxy resin comprises at least one dihydric phenol of the structure of formula (VI):

wherein R' is a divalent hydrocarbon radical of a dihydric phenol, and p is an average value between 0 and about 7.

10. The amine-epoxy composition of claim 5, wherein the at least one multifunctional epoxy resin comprises at least one of the diglycidyl ethers of bisphenol-A, the advanced diglycidyl ethers of bisphenol-A, and the diglycidyl ethers of bisphenol-F.

11. The amine-epoxy composition of claim 10, wherein the at least one multifunctional epoxy resin is represented by the structure of formula (VII):

wherein R" is H or $CH_3$, and p is an average value between 0 and about 7.

12. The amine-epoxy composition of claim 5, wherein the epoxy component further comprises a monofunctional epoxide.

13. The amine-epoxy composition of claim 4, wherein the stoichiometric ratio of epoxy groups in the epoxy component to amine hydrogens in the curing agent composition ranges from 1.5:1 to 0.7:1.

14. An article of manufacture comprising the amine-epoxy composition as set forth in claim 4.

15. The article of manufacture of claim 14, wherein the article is a coating, an adhesive, a construction product, a flooring product, or a composite product.

16. A method for producing the phenalkamine of claim 1 comprising the steps of reacting cardanol, triaminononane and an aldehyde.

17. The method of claim 16 wherein the mole ratio of cardanol to triaminononane is within the range of from 1:1 to 1:3 and the mole ratio of triaminononane to aldehyde is within the range of from 1:1 to 1:6.

18. The method of claim 16 wherein the aldehyde is selected from the group consisting of formaldehyde, paraformaldehyde, acetaldehyde, propionaldehyde, butyraldehyde, pentanal, hexanal, octanal, heptanal, decanal, benzaldehyde, cyclopentanecarboxaldehyde, and cyclohexanecarboxaldehyde.

19. A method for producing the curing agent composition of claim 2 comprising combining a phenalkamine of formula (IV) and an additional amine having at least two amine functionalities.

* * * * *